United States Patent [19]

Knapp et al.

[11] Patent Number: 5,194,587

[45] Date of Patent: Mar. 16, 1993

[54] MALARIA-SPECIFIC DNA SEQUENCES, EXPRESSION PRODUCTS THEREOF, AND THE USE THEREOF

[75] Inventors: Bernhard Knapp, Marburg-Schröck; Erika Hundt, Marbur-Wehrshausen; Burkhard Enders; Hans Küpper, both of Marburg, all of Fed. Rep. of Germany

[73] Assignee: Behringwerke Aktiengesellschaft, Marburg/Lahn, Fed. Rep. of Germany

[21] Appl. No.: 723,668

[22] Filed: Jun. 27, 1991

Related U.S. Application Data

[63] Continuation of Ser. No. 290,942, Dec. 28, 1988, abandoned.

[30] Foreign Application Priority Data

Dec. 30, 1987 [DE] Fed. Rep. of Germany ....... 3744495
Sep. 15, 1988 [DE] Fed. Rep. of Germany ....... 3831351

[51] Int. Cl.$^5$ ..................... C07K 13/00; C07K 15/04; A61K 39/015
[52] U.S. Cl. .................................. 530/324; 530/350; 530/820; 530/806; 424/88; 435/69.7
[58] Field of Search ............... 530/350, 387, 820, 806; 436/517; 514/2, 12; 424/88; 435/69.7

[56] References Cited

FOREIGN PATENT DOCUMENTS 0309746 4/1989 European Pat. Off. .

OTHER PUBLICATIONS

B. Knapp, et al., J. Biol. Chem. 266(11):7148-54(1991). Demonstration of Alternative Splicing of a Pre-mRNA Expressed in the Blood Stage Form of *Plasmodium falciparum*.
Perrin, L. H. et al. May 1985. J. Clin. Invest. 75:1718-1721. "Immunization with a *P. falciparum* Merozoite Surface Antigen . . . ".
Siddiqui, W. A. et al. May 1987. PNAS (USA) 84:3014-3018. "Merozoite Surface Coat Precursor Protein Completely Protects . . . ".
*Methods In Enzymology*, vol. 92. 1983 Academic Press. "Immunochemical Techniques".
*Methods in Enzymology*, vol. 93. 1983. Academic Press. "Immunochemical Techniques".
European Search Report for EP 88 12 1299.
M. J. McGarvey et al.,. PNAS USA 81:3690-3694 (1984).
L. H. Perrin et al., J. Exp. Med. 160:441-451 (1984).
L. H. Perrin et al., Clin. Exp. Immunol. 56:67-72 (1984).
L. S. Ozaki et al., J. Immunol. Meth. 89:213-219 (1986).
Promega Biotec, Immunoscreening System, Technical Manual (1986).
E. Y. Chen and P. H. Seeburg, DNA 4:165-170 (1985).
W. Trager and J. Jensen; Science 193:673-675 (1976).
C. Lambros and J. Vanderberg, J. Parasitol. 65:418-420 (1979).
G. Pasvol et al., Ann. Trop. Med. Parasitol. 72:87-88 (1978).
D. A. Johnson et al., Gene. Anal. Techn. 1:3-8 (1984).
P. Oquendo et al., Mol. Biochem. Parasitol. 18:89-101 (1986).
B. Perbal, A Practical Guide to Molecular Cloning (1984).
T. V. Huynh et al., DNA Cloning, 1:49-88 (1985).

(List continued on next page.)

*Primary Examiner*—Christine M. Nucker
*Assistant Examiner*—Thomas M. Cunningham
*Attorney, Agent, or Firm*—Finnegan, Henderson, Farabow, Garrett and Dunner

[57] ABSTRACT

The invention relates to malaria-specific DNA sequences, to the expression products thereof, and to the use thereof.

A combination of three of the expression proteins whose DNA sequences were isolated by screening a lambda gt11 gene bank with a monospecific antiserum against the protective 41kD antigen bend from *P. falciparum* protects Aotus monkeys completely from a *P. falciparum* infection in model experiments.

3 Claims, 1 Drawing Sheet

OTHER PUBLICATIONS

T. Maniatis et al., Molecular Cloning, A Laboratory Manual (1982).
R. W. Davis et al., Advanced Bacterial Genetics (1980).
F. Sanger et al., Proc. Natl. Acad. Sci. USA 74:5463–5467 (1977).
T. Triglia et al., EMBO J. 6:1413–1419 (1987).
J. L. Weber, Gene 52:103–109 (1987).
F. M. Ausubel et al., Eds., Current Protocols in Molecular Biology (1987).
K. Strebel et al., J. Virol. 57:983–991 (1986).
E. Remaut et al., Gene 15:81–93 (1981).
H. Kupper et al., Genetics of Industrial Microorganisms pp. 222–226.
Y. Ikeda and T. Beepu eds., (1982).

MALARIA-SPECIFIC DNA SEQUENCES, EXPRESSION PRODUCTS THEREOF, AND THE USE THEREOF

This application is a continuation of application Ser. No. 07/290,942 filed Dec. 28, 1988, now abandoned.

BACKGROUND OF THE INVENTION

An important step towards the development of a vaccine against malaria is the identification of protective antigens. In general, the antigens categorized as protective are those which have provided protection from *P. falciparum* infection administered intravenously in in vivo experiments in an animal model such as, for example, in Saimiri or Aotus monkeys. Only unsatisfactory protection experiments have hitherto been described in humans, but several isolated *P. falciparum* proteins have shown a complete or partial protective effect in an animal model. This applies both to protein fractions of 75 kD and 100 kD purified by gel electrophoresis and to the protein bands of molecular weights 200 kD, 140 kD and 41 kD purified by gel electrophoresis (L. H. Perrin et al. (1984), Clin. exp. Immunol. 56, 67–72; L. H. Perrin et al. (1985), J. Clin. Invest 75, 1718–1721; W. A. Siddiqui et al. (1987), Proc. Natl. Acad. Sci., USA 84, 3014–3018). Of the proteins which are specific for merozoites and have been prepared to date by biotechnological methods, a partial protective effect in immunization experiments with Saimiri or Aotus monkeys has been shown by a recombinant expression protein of the 5' repeat region of the so-called RESA 155 kD merozoite protein as well as by a synthetic oligopeptide of the 200 kD merozoite surface precursor protein and by a combination of synthetic oligopeptides of proteins of molecular weights 35 kD, 55 kD and 200 kD. Recombinant proteins, prepared by genetic manipulation, of the above antigens, which display a protective effect in in vivo experiments with monkeys, are potential candidates for a malaria vaccine.

The aim of the investigations was to isolate coding sequences for the protective 41 kD antigen band described by L. Perrin (1985 loc. cit.), to bring about the expression of the sequences, and to test the expression products for their protective effect in the monkey model. A specific antiserum against the 41 kD antigen band was used to isolate from a genomic expression bank fifteen clones and to elucidate the structure of their insertions. The sequences of the clones 41-1 to 41-10 and 41-12 to 41-15, as well as 41-17, are depicted in Tab. 1-15. Two clones (41-2 and 41-7) with very intense immunological reactions were used to isolate mono-specific antibodies from the serum used for the screening. These antibodies react specifically in the Western blot with a merozoite antigen of 41 kD.

In the Southern blot, a 3.0 kb EcoRI fragment and a 2.0 kb Sau3A fragment hybridized with the insert DNA of the clone 41-2. Both DNA fragments were isolated and sequenced.

The Sau3A fragment contains the complete coding region of the 41-2 gene. This region contains no introns and codes for 184 amino acids with a molecular weight of 21512 D. The 41-2 protein possesses a signal sequence and two further hydrophobic sections. No repetitive sequence portions are present. Western blot analysis of schizont proteins with rabbit antisera prepared against an expression product which contains 70% of the coding region produced a band of 29 kD. Furthermore, an mRNA of 1.6 kb was detected by Northern blot analysis.

On the other hand, the insert DNA of the clone 41-7 codes for the 41 kD protein. Rabbit antisera prepared against a fusion protein of 41-7 unambiguously recognize a 41 kD band in the Western blot. It was possible, by screening a genomic lambda gt11 EcoRI* gene bank with the insert DNA of the clone 41-7, to identify a clone which contains a malaria-specific insert of 2.3 kb. This was isolated and sequenced. It contains the complete coding region for a 41 kD protein. The gene does not encode a signal sequence and contains neither introns nor repetitive sections. The derived amino acid sequence of the 41 kD protein from *P. falciparum* is highly homologous (>60%) with aldolases from muscle and liver of mammals and with the aldolase from Trypanosoma brucei. In contrast to the mammalian genome, only one aldolase gene per genome was found by Southern blot analyses for *P. falciparum*.

The clones 41-1, 2, 3, 4, 5, 6, 7, 8, 9, 10, 12, 13, 14, 15 and 17 were detected on the basis of their cross-reactivities with the antiserum against the 41 kD protein band. They are suitable for the preparation of a vaccine. Expression of the insert DNAs of the clones 41-1 to 41-5 and 41-7, 41-10 and 41-14 was brought about in the vector pEX-31, and the resulting fusion proteins were purified. A combination of an immunologically effective amount of three expression products (41-1, 41-2 and 41-3) protects Aotus monkeys from *P.falciparum* infection.

SUMMARY OF THE INVENTION

Consequently, the invention relates to
a) the purified and isolated DNA sequences of the clones 41-1 to 41-10, 41-12 to 41-15 and 41-17, as well as 41-2gen and 41-7gen, including their transcription products,
b) DNA structures and vectors containing these sequences in whole or in part,
c) pro- or eukaryotic cells transformed with such DNA,
d) the polypeptides, or parts thereof, expressed by these cells by reason of the transformation,
e) the amino acid sequences thereof,
f) antibodies against the polypeptides under (d), including the use thereof for passive immunization, for diagnosis and for purifying said polypeptides,
g) vaccines against malaria which contain the amino acid sequences from (e) alone or in combination,
h) a process for the preparation, by genetic manipulation, of the polypeptides, or parts thereof, detailed under (d),
i) and the use of the said amino acid sequences for diagnosis.

Further embodiments of the invention are detailed in the examples and tables which follow and in the patent claims.

DETAILED DESCRIPTION OF PREFERRED EMBODIMENTS

Examples

Example 1

Screening of a lambda gt11 expression bank using the monospecific anti-41 kD serum $10^6$ PFU (plaque-forming units) of a genomic lambda gt11 expression (prepared from DNA of the *P. falciparum* strain T996) were screened with an antiserum against the 41 kD antigen band (L. H. Perrin et al. (1985) loc. cit.) from the *P. falciparum* strain SGE2 by known methods (L. S. Ozaki (1986), J. Immun. Method. 89, 213–219; Promega Biotec (1986), Proto Blot Immunoscreening System, Technical Manual). The detection system used for this was an antirabbit IgG/alkaline phosphatase conjugate (Promega, Order No. P 3731).

The screening of the genomic lambda gt11 gene bank with the antiserum against the 41 kD protein band made it possible to identify two very intensely reacting clones (41-2 and 41-7) and thirteen other clones which reacted more weakly (41-1, 41-3, 41-4, 41-5, 41-6, 41-8, 41-9, 41-10, 41-12, 41-13, 41-14, 41-15 and 41-17) and about 40 other very weakly reacting clones. The insert DNAs of the fifteen clones, which amount to 140bp to 650bp, were cut out with EcoRI and cloned into the EcoRI site of the vector pUC8 for further characterization.

Example 2

Sequencing of the insert fragments of clones 41-1 to 41-10, 41-12 to 41-15 and 41-17

The insert DNAs were sequenced by the dideoxy method using a primer and a reverse primer directly from the pUC8 plasmids (E. Y. Chen and P. H. Seeburg (1985), DNA 4, 165–170).

Tables 1–15 show the malaria-specific DNA sequences, and the amino acid sequences derived therefrom, of the clones 41-1, 41-2, 41-3, 41-4, 41-5, 41-6, 41-7, 41-8, 41-9, 41-10, 41-12, 41-13, 41-14, 41-15 and 41-17 in the only possible open reading frames. There are no overlaps or homologies whatever in these 15 sequence sections. The UWGCG (University of Wisconsin, Genetic Computer Group) program was used to examine these 15 sequences for homologous sequence sections within the EMBL data bank. None of these 15 partial sequences or relatively large homologous sections have hitherto been described. There is merely a 74% homology of nucleotides 1 to 134 in the sequence of the clone 41-10 with a partial sequence from nucleotide 2144 to 2274 in the 140 kD protein gene, as proposed in the Application DE-P 3,741,057. The sequence of the clone 41-10 is also the only one which contains repetitive sequence sections typical of *P. falciparum* proteins. The amino acid sequence of this clone includes three tetrapeptides of the sequence Pro-Ser-Glu-Ser, with the second serine residue in the second repeat being replaced by an asparagine residue, caused by a G-A transition. In addition, the sequence of the clone 41-7 from nucleotide 50 to 163 is 56% homologous with an aldolase mRNA from nucleotide 218 to 331 of the rat (T. Mucai et al. (1986), J. Biol. Chem. 261, 3347–3354).

Example 3

Detection of the 41 kD antigen using specific antibodies against the expression clones 41-2 and 41-7

The method of L. S. Ozaki (1986, loc. cit.) was used to isolate from the antiserum against the 41 kD protein band antibodies which are directed specifically against the products of the expression clones 41-1, 41-2, 41-3, 41-7, 41-8 and lambda gt11 (control). To obtain schizonts, *P. falciparum* was cultivated in human erythrocytes (W. Trager and J. B. Jensen (1976), Science 193, 673–675) and synchronized by treatment with sorbitol (C. Lambros and J. P. Vanderberg (1979), J. Parasitol. 65, 418–420). The schizonts were enriched to about 90% by flotation in Gelafundin ® (Braun Melsungen) (in analogy to G. Pasvol et al. (1978), Ann. Trop. Med. Parasitol. 72, 87–88). The schizonts were removed by centrifugation, washed, heated at 100° C. in SDS sample buffer for 5 min, treated with ultrasound, and frozen in aliquots.

Aliquots of the schizont solution were used for Western blot analysis of the abovementioned specific antibodies (D. A. Johnson et al. (1984) Gene Anal. Tech. 1, 3–8). In this the antibodies which were isolated using the expression clones 41-2 and 41-7 reacted very intensely with a 41 kD antigen band from schizonts.

Example 4

Cloning of a DNA fragment which contains the genetic information of the clone 41-2

15 µg of genomic DNA of the *P. falciparum* strain FCBR, which had been obtained by lysis of schizont cultures followed by ethidium bromide/CsCl centrifugation (P. Oquendo et al. (1986) Molecular and Biochemical Parasitology 18, 89–101), were digested with the restriction enzyme EcoRI, blotted onto Gene Screen membranes (Dupont) in accordance with the manufacturer's instructions, and then hybridized with nick-translated insert DNA of the clone 41-2 with a specific activity of $10^7$ to $10^8$ dpm/µg. After the filter had been washed in 0.3×SSC (1×SSC=0.15 M NaCl, 0.015 M Na citrate) and 1% SDS (sodium dodecyl sulfate) at 65° C. for 1 h, the filters were autoradiographed. This Southern blot experiment was used to identify a genomic EcoRI fragment which is about 3 kb in size and hybridizes with the insert DNA of the clone 41-2. 60 µg of P. falciparum DNA of the strain FCBR which had been cut with the restriction enzyme EcoRI were fractionated in a preparative gel, and the region from 2.8 kb to 3.2 kb was cut out and electroeluted (B. Perbal (1984), A Practical Guide to Molecular Cloning). This DNA was cloned by the method of T. V. Huynh et al. (in DNA cloning Vol. I, ed D. M. Glover (1985), 49–88) into the vector lambda gt10. $10^5$ PFU of the resulting gene bank were screened with nicktranslated insert DNA of the clone 41-2 by known methods (T. Maniatis et al. (1982), Molecular Cloning, A Laboratory Manual). This resulted in several phage clones which hybridized with the insert DNA of the clone 41-2. The phage DNA of one of these clones was isolated (R. W. Davis et al. (1980), A Manual for Genetic Engineering, Advanced Bacterial Genetics) and digested with the restriction enzyme EcoRI; a DNA fragment 3.0 kb in size was purified by gel electrophoresis and subcloned into the EcoRI restriction site of the vector pUC18 (plasmid pUC 41-2gen). In the subsequent Southern blot analysis (T. Maniatis et al., loc. cit.), this 3.0 kb EcoRI DNA fragment of pUC 41-2gen hybridized with the insert DNA of the clone 41-2.

Example 5

Sequence analysis of the clone pUC 41-2gen

The plasmid DNA pUC 41-2gen was sequenced starting from the EcoRI edge sites and using a primer and reverse primer (E. Y. Chen and P. H. Seeburg (1985) loc. cit.). From this it was possible to determine about 250 bases from each of the ends of the 3.0 kb EcoRI fragment. The sequence of one of these ends is identical to the insert DNA of the clone 41-2. To construct a restriction map, 0.5 μg samples of the isolated 3.0 kb EcoRI DNA fragment were incubated with various restriction enzymes, fractionated by gel electrophoresis, blotted onto nitrocellulose and hybridized with nick-translated insert DNA of the clone 41-2 by known methods (T. Maniatis, loc. cit.). The size of the restriction fragments to be hybridized made it possible to deduce the distance of various restriction cleavage sites from the EcoRI cleavage site, which is common to the two clones 41-2 and pUC 41-2gen. Based on the restriction map constructed in this way, restriction fragments of the clone pUC 41-2gen were isolated and subcloned into the phage vectors M13mp18 and M13mp19 for sequencing (F. Sanger et al (1977), Proc. Natl. Acad. Sci. USA, 74, 5463-5467). From this, the sequence was determined from the EcoRI restriction site, which belongs to the gene, in the direction towards the 5' end of the gene up to a DraI restriction cleavage site. Table 16 shows the DNA sequence and the derived amino acid sequence of this DraI-EcoRI DNA fragment comprising 1230bp of the clone pUC 41-2gen. The sequence from position 1036 to 1228 is identical to the insert DNA of 41-2. Since the sequence of the clone 41-2 and the genomic sequence of the clone pUC 41-2gen derive from different *P. falciparum* strains (strain T996 from Thailand and strain FCBR from Colombia), it appears that at least this gene section is highly conserved. The open reading frame of this sequence begins in position 784 with an ATG start codon and terminates with a TTC codon which belongs to the EcoRI restriction cleavage site within the gene. This part codes for the 149 N-terminal amino acids of the protein. The partial sequence of this gene has no repetitive sequence segments. The derived amino acid sequence begins with a sequence section of 18 amino acids, of which 4 are acidic and 5 are basic. This sequence section is followed by a hydrophobic part which is composed of 11 residues and is flanked on both sides by acidic amino acid residues. This hydrophobic region might function as a signal sequence. The region with basic and acidic amino acids in front of this putative signal sequence is relatively long; however, regions of similar length have also been described for other *P. falciparum* proteins (T. Triglia et al. (1987), The EMBO Journal 6, 1413-1419). The derived amino acid sequence was examined, using the UWGCG program, for hydrophilic regions and surface regions as well as for potential immunogenic epitope regions. This revealed three hydrophilic regions of the protein which are encoded by the nucleotide sequences of positions 890 to 907, 1079 to 1093 and 1151 to 1168.

The 5' non-coding region of the gene is extremely AT-rich (AT content=88.8%), as has also been described for other *P. falciparum* genes (J. L. Weber (1987), Gene 52, 103-109), and has in each case more than 15 stop codons in each of the three reading frames. Furthermore, a possible CAAT box is present in position 274, and a possible TATA box is located 64 nucleotides downstream of this. These structures might specify a possible promoter region for this gene.

Example 6

Isolation of the complete gene for 41-2

The sequence analysis of the clone pUC 41-2gen revealed a Sau3A cleavage site 947 bp away from the EcoRI cleavage site. Southern blot analysis of the genome identified a Sau3A fragment which is 2.0 kb in size and hybridizes with the insert DNA of the clone 41-2 (cf. Example 4). Hence this Sau3A fragment ought to have about 1050 bp of the genetic information of the 41-2 gene in the 3' direction from the EcoRI site. 60 μg of DNA from the strain FCBR which has been cut with the restriction enzyme Sau3A were fractionated in a preparative gel, and DNA fragments of 1.8 kb to 2.2 kb were isolated. This DNA was cloned into the XhoI site of the vector lambda ZAP as stated by the manufacturer (Stratagene). $10^5$ PFU of this gene bank were screened with nick-translated insert DNA of the clone 41-2, and about 40 phage clones were identified (cf. Example 4). By automatic excision using the Stratagene method, a bluescript vector (pSK- 41-2gen) was isolated from one of these phage clones. Restriction of this plasmid DNA with KpnI and EcoRI resulted in the isolation of two DNA fragments of 950 bp and 1050 bp, of which the 950 bp fragment hybridized in the Southern blot with the insert DNA of the clone 41-2. The plasmid pSK- 41-2 DNA was sequenced using a primer and reverse primer (E. Y. Chen and P. H. Seeburg (1985) loc. cit.). The sequence determined using the primer is identical to the sequence of the insert DNA of the plasmid pUC 41-2gen from the Sau3A site in the 3' direction. The 1050 bp EcoRI DNA fragment of the plasmid pSK- 41-2gen was subcloned into the EcoRI site of the vector pKS+ (T Maniatis et al., loc. cit.). A restriction map of this DNA fragment was constructed. Based on this map, restriction fragments were subcloned into the bluescript vectors and, after ssDNA preparation, sequenced (Stratagene instruction manual). This entailed the sequence being completely determined from the EcoRI restriction site of the 41-2 gene in the 3' direction as far as the Sau3A site. Table 17, which is a continuation of Table 16, shows the DNA sequence and the derived amino acid sequence of this EcoRI-Sau3A DNA fragment, which comprises 1050 bp, of the clone pSK- 41-2gen. This gene section now codes for only 35 additional amino acids until a TAG stop codon supervenes. The 3' non-coding region of the gene is extremely AT-rich (AT content=84.7%) and contains more than 11 stop codons in each of the three reading frames. The S1 mapping technique (F. M. Ausubel et al. (1987), Current Protocols in Molecular Biology, Harvard Medical School, Boston) revealed no evidence whatever of an intron-exon structure of this gene. Finally, Northern blot analysis (T. Maniatis et al.,.loc. cit.) detected an mRNA of the schizont stage with a size of 1.6 kb. It is therefore necessary to assume that the 41-2 gene has only a single coding section of 552 bp (AT content=73%). The latter codes for an antigen of 21512 Dalton, which has a signal sequence (cf. Example 5) but no repetitive sections. Besides the signal sequence, this antigen has two further hydrophobic sections in amino acid positions 73 to 85 and 130 to 147, which may have a membrane-anchoring function.

Example 7

Expression of the inserts of the clones 41-1 to 41-5 and 41-7, 41-10 and 41-14 in the vector pEX31

The insert fragments of the clones 41-1 to 41-5, 41-7, 41-10 and 41-14 were, after restriction with EcoRI, isolated by gel electrophoresis, ligated into a vector pEX31b which had been digested with the restriction enzyme EcoRI and dephosphorylated (K. Strebel et al. (1986) Journal of Virology 57, 983-991), and transformed into competent C600 bacteria containing the plasmid pCI857 (F. Remaut et al. (1981), Gene 15, 81-93). Individual colonies were examined by SDS-PAGE for expression of the Plasmodia-specific DNA sequences as MS2 polymerase fusion proteins. Induction was effected by increasing the temperature by the method of H. Küpper et al. (in Y. Ikeda and T. Beppu (ed). Proceedings of the Fourth International Symposium on Genetics of Industrial Microorganisms (1982), Kyoto Kodansha Ltd., Tokyo). Expression of all 8 fragments was possible in high yield.

Example 8

Purification of the expression products

Cultures of transformed bacteria were each shaken vigorously in 1 l of LB medium containing 50 pg/ml of ampicillin and 25 pg/ml kanamycin at 28° C. for 20 h. Addition of 4 l of LB medium which had been heated to 42° C. was followed by renewed shaking at 42° C. for 4 h. The bacteria were removed by centrifugation, resuspended in 200 ml of phosphate-buffered saline (PBS) and disrupted mechanically. The soluble proteins were removed by centrifugation, and the sediments which contained the expression products were washed twice with PBS and then washed successively with increasing urea concentrations (from 1 M to about 5 M) until the fusion proteins dissolved. Subsequently, dialysis was carried out with decreasing urea concentrations until the urea concentration which sufficed to keep the expression products in solution was reached. This process resulted in a purity of 60-80%.

Example 9

Detection of the antigen encoded by 41-2gen

It was not possible, using rabbit antisera directed against the expression product of the clone 41-2, unambiguously to detect malaria antigen in the Western blot with schizont proteins. Therefore the aim was to express a larger DNA fragment of the gene 41-2. For this purpose, the restriction enzymes AluI and EcoRI were used to isolate a 388 bp fragment of the 41-2 gene which contains 70% of the coding region. This fragment was subcloned in the SmaI and EcoRI sites of the plasmid pUC18. The restriction enzyme EcoRI was used to isolate from this plasmid a 401 bp fragment, which was cloned into the EcoRI site of the vector pEX31b. After transformation it was possible to identify bacterial colonies which express a fusion protein of 26 kD (cf. Example 7). This was purified (cf. Example 8) and used for immunizing rabbits. The antisera recognized, in the Western blot with schizont proteins, a 29 kD antigen which is encoded by the 41-2 gene. The difference between the calculated molecular weight of 22 kD and the molecular weight of 29 kD in SDS polyacrylamide gels can be explained by secondary modification. Thus, the protein has an N-gly-cosylation site in the asparagine residue in position 166.

Confirmation that the clone 41-2 encodes a very small antigen is obtained from Northern blot analysis. Thus, there was detected in the schizont stage of P.falciparum a mRNA of 1.6 kb which hybridizes with the insert DNA of the clone 41-2. Northern blot analysis was carried out by known methods (T. Maniatis et al., loc. cit.).

Example 10

Assignment of antigens of other clones

Antisera against the purified fusion proteins of the clones 41-1, 41-3, 41-4, 41-5, 41-7 and 41-10 were used to identify the corresponding antigens by Western blot analysis with schizont proteins. In this, the antisera against the fusion proteins of the clones 41-1, 41-3 and 41-4 did not allow unambiguous identification. The insert DNA of the clone 41-5 can be assigned to a 96 kD antigen. A group of three 96 kD antigens of P.falciparum has been described (H. Jouin et al. (1987), Inf. Imm. 55, 1387-1392). Antisera directed against an expression product of the clone 41-10 recognize two antigens of 113 and 140 kD. The reaction with the 113 kD antigen was identified as a cross-reaction with the SERPI antigen (cf. Example 2) which is identical to a protective antigen. 41-10 thus encodes a 140 kD protein of P.falciparum.

It is common to all these genes that the antigens, or parts thereof, encoded by them, react with a serum which is directed against a 41 kD protein band which has a protective action. Only the clone 41-7, which, together with the clone 41-2, has the strongest reactivity with the antiserum against the 41 kD protein band, can be unambiguously assigned to a 41 kD protein.

In the Western blot with schizont proteins, antisera directed against the fusion protein of the clone 41-7 unambiguously recognize the 41 kD protein band, which is also recognized by the starting serum. This clone thus appears to encode a subfragment of the 41 kD antigen. Confirmation that the investigated clones harbor partial sequences of various genes was moreover obtained by Southern blot analyses for the clones 41-1, 41-2, 41-3, 41-7, 41-10, 41-14 and 41-15.

Example 11

Preparation of a genomic lambda gt11 gene bank

2 μg of DNA from the P.falciparum strain FCBR were incubated at 37° C. overnight with 14 units of the restriction enzyme EcoRI in 10 mM tris-HCl (pH 7.5), 10 mM MgCl$_2$, 1 mM dithiothreitol and 40% glycerol, and fractionated by gel electrophoresis. Under these conditions, the restriction enzyme shows EcoRI asterisk activity, resulting in the formation of DNA fragments from about 50 bp to 10 kb. The DNA region between 500 bp and 7 kb was electroeluted and cloned by the method of T. V. Huynh et al. (1985; in DNA cloning Vol. I, a practical approach, ed. D. M. Glover) into the vector lambda gt11. A gene bank of $5 \times 10^5$ recombinant phage clones was prepared and was amplified.

Example 12

Isolation and sequencing of the 41-7 gene

Since the clone 41-7 actually codes for a subfragment of a 41 kD protein (cf. Example 10), the aim is to isolate the complete gene. For this purpose, the genomic lambda gt11 EcoRI* gene bank (cf. Example 11) was screened by known methods (T. Maniatis et al., loc. cit.) with nick-translated insert DNA of the clone 41-7. This resulted in three lambda gt11 clones from each of which it was possible to isolate, using the restriction enzymes EcoRI and SalI, an insert 3.3 kb in size. The malaria-specific portion of the insert amounts to 2.3 kb. A restriction map of this DNA fragment was constructed. Based on this, subfragments were cloned into the bluescript vectors (Stratagene) for sequencing. It was possible to elucidate the complete DNA sequence of this malaria-specific fragment which is 2.3 kb in size. Table 18 shows the DNA sequence of the 41-7 gene, with the amino acid sequence derived therefrom. The gene has no introns. 525 base-pairs of the 5' non-coding region were ascertained (AT content = 84.2%), as were 772 base-pairs of the 3non-coding region (AT content = 84.2%). The central section comprises 1086 base-pairs (AT content = 64.4%) and codes for 362 amino acids. The calculated molecular weight of 39314 D for this gene agrees well with the molecular weight of 41 kD determined by gel electrophoresis. This gene is transcribed into an mRNA which is 2.4 kb in size, as was ascertained by Northern blot analysis by known methods (T. Maniatis et al. loc. cit.). It was possible to deduce by Southern blot analysis (cf. Example 4) that only one copy of this gene exists in each P.falciparum genome. It was also found that this gene is conserved in various P.falciparum strains (FCBR from Colombia, Palo Alto from Uganda, SGE2 from Zaire, ItG$_2$G$_1$ from Brazil, and FVOR from Vietnam). In addition, the malaria-specific DNA sequence of the clone 41-7 (strain T996 from Thailand) is identical to the partial sequence from position 464 to 729 of the gene isolated from the FCBR strain. Thus the clone 41-7 codes for the 88 N-terminal amino acids of the 41 kD protein.

It is evident from the derived amino acid sequence that the 41 kD protein contains no signal sequence and no repetitive sections. The UWGCG (University of Wisconsin, Genetic Computer Group) program was used to examine this amino acid sequence for homologous proteins within the NBRF protein data bank. It was found from this that the 41 kD protein is 66% homologous with human liver aldolase (M. Mukai et al., (1985), Nucleic Acid Res. 13, 5055–5069), 66% homologous with rat liver aldolase (K. Tsutsami et al, (1984) J. Biol. Chem. 259, 14572–14575), 68% homologous with rabbit muscle aldolase (D. R. Tolan et al. (1984), J. Biol. Chem. 259, 1127–1131) and 61% homologous with the aldolase from *Trypanosoma brucei* (C. E. Clayton (1985) EMBO J. 4, 2997–3003). The 41 kD protein thus appears to be the P.falciparum aldolase.

Example 13

Experimental protection in an animal model: immunization of Aotus lemurinus griseimembra (karyotype VI)

This experiment was carried out to test the described expression products for their efficacy in inducing protective immunity in monkeys susceptible to P.falciparum. The vaccine used in the experiment was a combination of the expression products of the immunologically strongly reacting clones 41-1, 41-2 and 41-3.

1. Design of experiment

6 Aotus monkeys of the abovementioned species (body weight 1,000–1,500 g, male and female animals bred by Behringwerke AG) were randomized and assigned to 2 groups each of 3 animals.

Fusion proteins of the clones 41-1, 41-2 and 41-3 were dissolved in 3 M urea in PBS and mixed in the ratio 1:1:1 (final concentration: 300 μg of protein/ml). 3 animals were immunized subcutaneously 3×, at intervals of 3 weeks, each time with 1 ml of the combined fusion proteins. A 10% admixture of 50% Al(OH)$_3$/45% lecithin/5% saponin to the antigen was used as adjuvant.

3 animals in the infection control group likewise each received an injection of 3 M urea in PBS+adjuvant without antigenic component in accordance with the above-mentioned scheme.

In order to ensure that the experimental P. falciparum infections of the animals were as near the same severity as possible, all the monkeys were splenectomized eight days after the last immunization (increased susceptibility).

On day 67 after the 1st vaccination, all 6 animals were infected intravenously with $5 \times 10^6$ parasitized erythrocytes. The strain chosen for challenge was P. falciparum Palo Alto (Uganda) which was adapted in vitro to Aotus erythrocytes and was transferred directly from a splenectomized donor animal (4% parasitemia) to the experimental animals. This strain is distinguished by high infectiosity compared with other P. falciparum isolates. It is also of interest to mention that this strain is heterologous in terms of provenance and serotype to the strain T996 (Thailand) used for obtaining the immunization antigens.

Physiological, parasitological, serological and clinicochemical parameters were examined regularly during the entire course of the study (before and after immunization and after the challenge).

2. Results

No pathological changes in any of the physiological (clinical manifestations, temperature, weight) or clinicochemical (erythrocytes, hematocrit, ESR, serum enzymes GPT and GOT) parameters investigated were seen throughout the immunization period. Additional drug-safety investigations (acute subcutaneous toxicity in the mouse, local tolerability in the monkey in accordance with the specifications of the European Pharmacopoeia) demonstrated adequate safety and tolerability of the vaccine preparation used.

2.1 Parasitemia

The main parameter for assessing the value of an induced protection is the detection under the microscope of parasitized erythrocytes in the peripheral blood of the experimental animal.

A few parasitized erythrocytes (less than 1 per thousand) were detectable in the Giemsa-stained blood smear from the non-immunized animals as early as 7–10 days after the infection. The appearance of parasites in the immunized animals was delayed to 10–15 days after infection, and they reached maximum parasitemias of 1–2% and controlled the infection spontaneously. There was one intercurrent death of an animal from pneumonia.

Whereas one animal in the non-immunized group was able itself to control a maximum parasitemia of 4.5%, it was necessary for the two other animals to be treated with mefloquine (Hoffmann La Roche) after a parasitemia of >10% had been reached, in order to prevent the infection taking a lethal course. The Palo Alto strain used for the challenge proved in preceding infection experiments to be chloroquine-resistant.

Figure 1A:
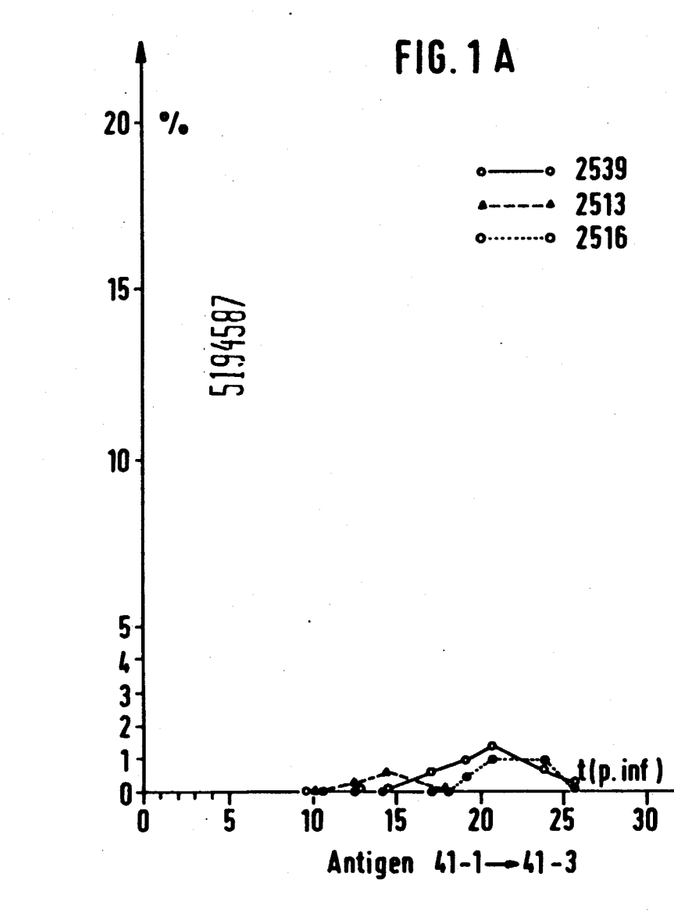
FIG. 1A depicts the course of parasitemia in 3 Aotus monkeys after immunization with a combination vaccine composed of fusion proteins of the clones 41-1, 41-2, and 41-3. The y-axis represents percentage of parasitemia; the abscissa represents time after infection.
Figure 1B:
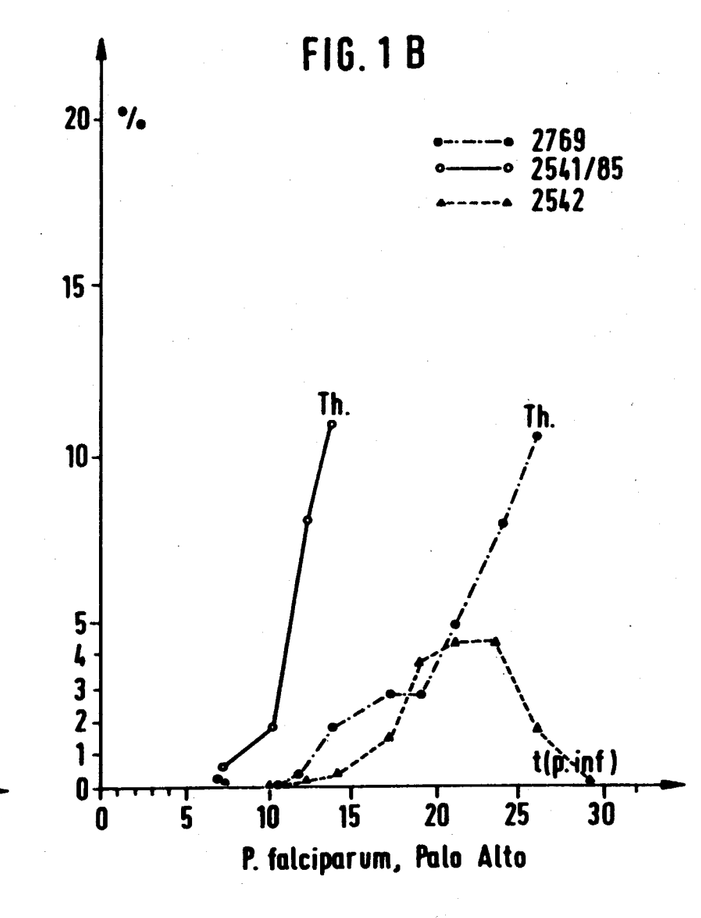
FIG. 1B depicts the course of parasitemia in 3 non-immunized Aotus monkeys.

FIG. 1 shows, on the left, the course of the parasitemia in Aotus monkeys after immunization with a combination vaccine composed of fusion proteins of the clones 41-1, 41-2 and 41-3 and, on the right, that of the control (non-immunized animals).

TABLE 1

Nucleotide sequence of the malaria-specific DNA insert of the clone 41-1, and derived amino acid sequence

```
             10                  30                    50
TAAAATCTTTATGTATTTTTAAACAAAGAAATAAAAAGGTAAGGTCATCAAATAATTCAT
 Lys Ser Leu Cys Ile  Phe Lys Gln Arg Asn Lys Lys Val Arg Ser Ser Asn Asn Ser S 70                  90                    110
CTTTCTTAATTGATTTTAGAAACTCACATACGAATAATATCAATATGTTAACAGAAAATC
er Phe Leu Ile  Asp Phe Arg Asn Ser His Thr Asn Asn Ile  Asn Met Leu Thr Glu Asn G 130                 150                   170
AAAAGTTTAATAATGTATTATTGAATAAAGAAATTCAGATGGATGAAAATCAGGAACGTG
ln Lys Phe Asn Asn Val Leu Leu Asn Lys Glu Ile  Gln Met Asp Glu Asn Gln Glu Arg G 190                 210                   230
AATTTTCAATTGATGATTGTTTAATGAACTGCCTGAAACATAATGCATCTAATTTAAAAA
lu Phe Ser Ile  Asp Asp Cys Leu Met Asn Cys Leu Lys His Asn Ala Ser Asn Leu Lys T 250                 270                   290
CCAATGAAGATTATGAAAGATATTGTAATGAAGACAAAATATTGAATCCAGATTATAAGC
hr Asn Glu Asp Tyr Glu Arg Tyr Cys Asn Glu Asp Lys Ile  Leu Asn Pro Asp Tyr Lys P 310                 330                   350
CTTCAGAATCTAGAAAACTGGGAGAAAAATTTTTGCAAAAAAGTCAAAAGGAATTATATT
ro Ser Glu Ser Arg Lys Leu Gly Glu Lys Phe Leu Gln Lys Ser Gln Lys Glu Leu Tyr T

370
ATTCTTATGC
yr Ser Tyr
```

TABLE 2

Nucleotide sequence of the malaria-specific DNA insert of the clone 41-2, and derived amino acid sequence

```
             10                  30                    50
AACATGTGTGGAAATATTTATTTCAGCATTCATCTGATTTACTTAAATCTCAAGATAGTA
 His Val Trp Lys Tyr Leu Phe Gln His Ser Ser Asp Leu Leu Lys Ser Gln Asp Ser I 70                  90                    110
TTTATGAGTATATGATATGTGATAAAAATATTTTATTAAATAAATTTATAAATGTACCAA
le Tyr Glu Tyr Met Ile  Cys Asp Lys Asn Ile  Leu Leu Asn Lys Phe Ile  Asn Val Pro L 130                 150                   170
AAGATTATGGAAATATAAATTGTGCTGCCTTTGCAGCAGGTATTGTTGAAGGCTTCCTCT
ys Asp Tyr Gly Asn Ile  Asn Cys Ala Ala Phe Ala Ala Gly Ile  Val Glu Gly Phe Leu C

190
GTAGTTCTGAATTC
ys Ser Ser Glu Phe
```

TABLE 3

Nucleotide sequence of the malaria-specific DNA insert of the clone 41-3, and derived amino acid sequence

```
             10                  30                    50
CAGTAAAAATTTTAAAAAAAAAGAAAAATTTAAGAAAAATAAAGGAAACCACTGATGAAG
 Val Lys Ile  Leu Lys Lys Lys Lys Asn Leu Arg Lys Ile  Lys Glu Thr Thr Asp Glu G 70                  90                    110
AGAAAACTTCAGATAATGTTTCTCAAATGTATGAAAGAAAAGGTGGACCATTACCACCAC
lu Lys Thr Ser Asp Asn Val Ser Gln Met Tyr Glu Arg Lys Gly Gly Pro Leu Pro Pro P

130
CCGAACTTAGAAAACA
ro Glu Leu Arg Lys
```

TABLE 4

Nucleotide sequence of the malaria-specific DNA insert of the clone 41-4, and derived amino acid sequence

```
             10                  30                    50
GTATACCTGAATTTTTAGGACAATATCATAATGTTCCCCATGTATTCAAAGATTATATGA
 Ile  Pro Glu Phe Leu Gly Gln Tyr His Asn Val Pro His Val Phe Lys Asp Tyr Met S 70                  90                    110
GTTCCAATGATTTTATAAGTGGTATAAATAATATAAATGAATCAGATGCTCTTTTTAATA
er Ser Asn Asp Phe Ile  Ser Gly Ile  Asn Asn Ile  Asn Glu Ser Asp Ala Leu Phe Asn A
```

TABLE 4-continued

Nucleotide sequence of the malaria-specific DNA insert of the clone 41-4, and derived amino acid sequence

```
                130                    150
ACATACAATATATAAACCAAGCGAATGACCAAGAAGAAAACAAATT
sn  Ile  Gln Tyr Ile   Asn Gln Ala Asn Asp Gln Glu Glu Asn Lys
```

TABLE 5

Nucleotide sequence of the malaria-specific DNA insert of the clone 41-5, and derived amino acid sequence

```
        10                     30                     50
TGTTTGATAATAGTGATTTTATTAAA TCAATAATGGATTCTAATAAACAATTAAAAAAGT
  Phe Asp Asn Ser Asp Phe Ile  Lys Ser Ile  Met Asp Ser Asn Lys Gln Leu Lys Lys L 70                     90                    110
TAAGAGAACAAAATTCTGATTTAAATCATATTTTAAATGATTCTCAGACTTTAAAACAAT
eu Arg Glu Gln Asn Ser Asp Leu Asn His Ile  Leu Asn Asp Ser Gln Thr Leu Lys Gln S 130                    150                    170
CTTTTGAAATGATTAAGAATCCATCTTTGATGAAAGAATTAATGAAAAATACTGATAGAG
er Phe Glu Met Ile  Lys Asn Pro Ser Leu Met Lys Glu Leu Met Lys Asn Thr Asp Arg A

190
CTATTAGTAATATTGAAGCCATACC
la Ile  Ser Asn Ile  Glu Ala Ile
```

TABLE 6

Nucleotide sequence of the malaria-specific DNA insert of the clone 41-6, and derived amino acid sequence

```
         10                     30                    50
TCGTTGTCCTTTCCTTTGGTGATAAACGCAATGAGATAAAACAAAAAATTGACACGTTTT
   Val Val Leu Ser Phe Gly Asp Lys Arg Asn Glu Ile  Lys Gln Lys Ile  Asp Thr Phe C 70                     90                    110
GTGGTGTAAGTAATGAAGAAAAGGAGAAACTAAAGGAACAATGGAAATGCTATGAAGCTA
ys Gly Val Ser Asn Glu Glu Lys Glu Lys Leu Lys Glu Gln Trp Lys Cys Tyr Glu Ala  L 130                    150
AATATGTAAAGGAAGATAATAAAAGTAAAG
ys Tyr Val Lys Glu Asp Asn Lys Ser Lys
```

TABLE 7

Nucleotide sequence of the malaria-specific DNA insert of the clone 41-7, and derived amino acid sequnce

```
          10                    30                    50
TGAATGCCCCAAAAAAATTACCAGCAGATGTTGCCGAAGAATTAGCAACCACCGCCCAAA
    Asn Ala Pro Lys Lys Leu Pro Ala Asp Val Ala Glu Glu Leu Ala Thr Thr Ala Gln L 70                    90                    110
AGCTTGTTCAAGCTGGAAAGGGAATTTTAGCTGCTGATGAATCAACACAAACCATTAAGA
ys Leu Val Gln Ala Gly Lys Gly Ile  Leu Ala Ala Asp Glu Ser Thr Gln Thr Ile  Lys L 130                   150                    170
AAAGATTCGACAACATCAAATTAGAGAACACAATAGAAAACAGAGCTAGCTACAGAGATT
ys Arg Phe Asp Asn Ile  Lys Leu Glu Asn Thr Ile  Glu Asn Arg Ala Ser Tyr Arg Asp L 190                   210                    230
TATTATTTGGAACTAAAGGATTAGGAAAATTCATTTCAGGAGCAATTTTATTTGAAGAAA
eu Leu Phe Gly Thr Lys Gly Leu Gly Lys Phe Ile  Ser Gly Ala Ile  Leu Phe Glu Glu T

250
CATTATTTCAAAAGAATGAAGCCGGT
hr Leu Phe Gln Lys Asn Glu Ala Gly
```

TABLE 8

Nucleotide sequence of the malaria-specific DNA insert of the clone 41-8, and derived amino acid sequence

```
         10                     30                    50
TAACATTTTCTGTAGATACAAAACAAAATTTAAATGCATCTTATTCTAGTGGACAAGAAA
   Thr Phe Ser Val Asp Thr Lys Gln Asn Leu Asn Ala Ser Tyr Ser Ser Gly Gln Glu A 70                     90                   110
ATAAACAAAATGAATCTGATGGAAAAGAAAATGAAGAAGATGAAGAAAATAAGGTATATG
sn Lys Gln Asn Glu Ser Asp Gly Lys Glu Asn Glu Glu Asp Glu Glu Asn Lys Val Tyr A
```

TABLE 8-continued

Nucleotide sequence of the malaria-specific DNA insert of the clone 41-8, and derived amino acid sequence

```
          130                   150                   170
ATTTAATACTGGAAAATATAGAACCTAACAAAAAAATACCCATCATAAAAATCGTTAAAG
sp Leu Ile Leu Glu Asn Ile Glu Pro Asn Lys Lys Ile Pro Ile Ile Lys Ile Val Lys G 190                   210                   230
AAATAAAAAAAGATCTTAATTTAAAACAAGCAAAGGATTTAGTTGATAATTTGCCACA
lu Ile Lys Lys Asp Leu Asn Leu Lys Gln Ala Lys Asp Leu Val Asp Asn Leu Pro
```

TABLE 9

Nucleotide sequence and derived amino acid sequence of the malaria-specific insert DNA of the clone 41-9

```
          10                    30                    50
AAAATAAAAATTATACAGGTAATTCTCCAAGTGAAAATAATAAGAAAGTTAACGAAGCTT
    Asn Lys Asn Tyr Thr Gly Asn Ser Pro Ser Glu Asn Asn Lys Lys Val Asn Glu Ala L 70                    90                    110
TAAAATCTTACGAAAATTTTCTCCCAGAAGCAAAAGTTACAACAGTTGTAACTCCACCTC
eu Lys Ser Tyr Glu Asn Phe Leu Pro Glu Ala Lys Val Thr Thr Val Val Thr Pro Pro G 130                   150                   170
AACCAGATGTAACTCCATCTCCATTATCTGTAAGGGTAAGTGGTAGTTCAGGATCCACAA
ln Pro Asp Val Thr Pro Ser Pro Leu Ser Val Arg Val Ser Gly Ser Ser Gly Ser Thr L 190                   210                   230
AAGAAGAAACACAAATACCAACTTCAGGCTCTTTATTAACAGAATTACAACAAGTAGTAC
ys Glu Glu Thr Gln Ile Pro Thr Ser Gly Ser Leu Leu Thr Glu Leu Gln Gln Val Val G 250                   270                   290
AATCACAAAATTATGACGAAGAAGATGATTCCTTAGTTGTATTACCCATTTTTGGAGAAT
ln Ser Gln Asn Tyr Asp Glu Glu Asp Asp Ser Leu Val Val Leu Pro Ile Phe Gly Glu S 310                   330                   350
CCGAAGATAATGACGAATATTTAGATCAAGTAGTAACTGGAGAAGCAATATCTGTCACAA
er Glu Asp Asn Asp Glu Tyr Leu Asp Gln Val Val Thr Gly Glu Ala Ile Ser Val Thr M 370                   390
TGGATAATATCCTCTCAGGATTTGAAAATGAATATGA
et Asp Asn Ile Leu Ser Gly Phe Glu Asn Glu Tyr
```

TABLE 10

Nucleotide sequence and derived amino acid sequence of the malaria-specific insert DNA of the clone 41-10

```
          10                    30                    50
AATCTCATTCTGACGAAAATATTGTAACTTTACAAGGAAAACTTAGAAATACAGCTATCT
    Ser His Ser Asp Glu Asn Ile Val Thr Leu Gln Gly Lys Leu Arg Asn Thr Ala Ile C 70                    90                    110
GTATAAAGAATGTTGATGAATGGATATTAAATAAAAGAGGTCTAACATTACCTAGTGAAT
ys Ile Lys Asn Val Asp Glu Trp Ile Leu Asn Lys Arg Gly Leu Thr Leu Pro Ser Glu S 130                   150
CACCTAATGAATCACCTAGTGAATCAGATAGTTATCTTAA
er Pro Asn Glu Ser Pro Ser Glu Ser Asp Ser Tyr Leu
```

TABLE 11

Nucleotide sequence of the malaria-specific DNA insert of the clone 41-12, and derived amino acid sequence

```
          10                    30                    50
ATGAAGGAGAAGAATTAATATTAAATGATGATCAAAATAAATTACATATTGATACATTTG
    Glu Gly Glu Glu Leu Ile Leu Asn Asp Asp Gln Asn Lys Leu His Ile Asp Thr Phe G 70                    90                    110
AAAAATACAAATATCTCATTTGTGAAAATATTAATAATGACAAATTTGTTATAAAAAATA
lu Lys Tyr Lys Tyr Leu Ile Cys Glu Asn Ile Asn Asn Asp Lys Phe Val Ile Lys Asn A 130                   150                   170
ATCAAATTACAACATTTGAAAACTTTTTGAAAAACCAACAAAATTTTGAAATAA
sn Gln Ile Thr Thr Phe Glu Asn Phe Leu Lys Asn Gln Gln Asn Phe Glu Ile
```

TABLE 12

Nucleotide sequence and derived amino acid sequence of the malaria-specific insert of clone 41-13.

```
                  20                         40                         60
TAAATAATGAAAATATGGATAAACAAAATGTTAATATTCAAAATGAAGGTAATGGTTTTA
   Asn Asn Glu Asn Met Asp Lys Gln Asn Val Asn Ile  Gln Asn Glu Gly Asn Gly Phe A 80                        100                        120
ATAATAATAAAAATAATAATGATCTTTTAAATGTTTATATATCACCTAATATGATTAATC
sn Asn Asn Lys Asn Asn Asn Asp Leu Leu Asn Val Tyr Ile  Ser Pro Asn Met Ile  Asn H 140                        160                        180
ATTCTTTATCTTCAACTTGTGAAAAAAAAAATAAAGAAGATAACAAAATGAATGACAATA
is Ser Leu Ser Ser Thr Cys Glu Lys Lys Asn Lys Glu Asp Asn Lys Met Asn Asp Asn L 200                        220                        240
AATTTCTTAATAGCAGTAGTAAAATGAAAATTCCAGAGATAAGTACGAACAACTCAAATG
ys Phe Leu Asn Ser Ser Ser Lys Met Lys Ile Pro Glu Ile  Ser Thr Asn Asn Ser Asn G 260                        280                        300
AAAAGATTGTTAATGTGTCAAATGATGAAATGTTAGTATATCATAATTTAACCGTATTAA
lu Lys Ile  Val Asn Val Ser Asn Asp Glu Met Leu Val Tyr His Asn Leu Thr Val Leu A 320                        340                        360
ATGTAAAGGAACAAGGAGGTGTAACAGAAGAATCGAGCTGTATAAAACGCACATATTTTG
sn Val Lys Glu Gln Gly Gly Val Thr Glu Glu Ser Ser Cys Ile  Lys Arg Thr Tyr Phe V 380                        400                        420
TGGATCAATTTTATGATTCATATAATATGAGAAATGAAAAAATAACAGATGATAATATGC
al Asp Gln Phe Tyr Asp Ser Tyr Asn Met Arg Asn Glu Lys Ile  Thr Asp Asp Asn Met G 440                        460                        480
AAGTAGAAGATATATATAATGTAAAGGAAAATATAAAAAGAACTCTAAAAGGTGATGGTC
ln Val Glu Asp Ile  Tyr Asn Val Lys Glu Asn Ile  Lys Arg Thr Leu Lys Gly Asp Gly P 500                        520                        540
CTGATGATGTCAAAACGAATATGCTGAGTGAAGATAATAGTTATGCAAGTGGTTTATGGG
ro Asp Asp Val Lys Thr Asn Met Leu Ser  Glu Asp Asn Ser Tyr Ala Ser Gly Leu Trp G 560                        580                        600
GTAACGAAATAAACTTTATTAGTAATAATGAAAATTGTTTAAATAGCTATGATATATCAT
ly Asn Glu Ile  Asn Phe Ile  Ser Asn Asn Glu Asn Cys Leu Asn Ser  Tyr Asp Ile  Ser C 620                        640
GTGATGAGAAATATATCCCAAATGAAGAGGAACAGGA
ys Asp Glu Lys Tyr Ile  Pro Asn Glu Glu Glu Gln
```

TABLE 13

Nucleotide sequence and derived amino acid sequence of the malaria-specific insert of clone 41-14.

```
                10                         30                         50
ACAACAATATGAACAGAATAAATAGTTTAAACAATAAAAATAATATTAACCCTATAAATC
   Asn Asn Met Asn Arg Ile  Asn Ser Leu Asn Asn Lys Asn Asn Ile  Asn Pro Ile  Asn G 70                         90                        110
AATACAATGATGAAAAACAAAACTTACTTAACGNCCATCTTCAGTYCAATCAAGTAAATT
ln Tyr Asn Asp Glu Lys Gln Asn Leu Leu Asn Xxx His Leu Gln Xxx Asn Gln Val Asn T 130                        150                        170
ATNATAATAACCTTGTGAATGGCYTTCATANAANNAAATTTTTAAGCAATAATAATTATA
yr Xxx Asn Asn Leu Val Asn Gly Xxx His Xxx Xxx Lys Phe Leu Ser Asn Asn Asn Tyr I 190                        210                        230
TTAATACTACAGATATTAATGGAAATAATATGATTAGTCATAATGATCATATGAATAATA
le Asn Thr Thr Asp Ile  Asn Gly Asn Asn Met Ile  Ser His Asn Asp His Met Asn Asn L 250                        270                        290
AATTATACAGTAATATAAACAATAATTATTATTATAATAGGGCTAACAATGAAATTCCTA
ys Leu Tyr Ser Asn Ile  Asn Asn Asn Tyr Tyr Tyr Asn Arg Ala Asn Asn Glu Ile  Pro A 310                        330                        350
ATAATAATAGTAACAATCATAATAATAATTTCAATATATATGAATCCAAATACCAAACCA
sn Asn Asn Ser Asn Asn His Asn Asn Asn Phe Asn Ile  Tyr Glu Ser Lys Tyr Gln Thr M 370                        390                        410
TGATTCATAACAACAACATAGGACAAGATCTAAAACAACAAATAAATAATTATAATGAAA
et Ile  His Asn Asn Asn Ile  Gly Gln Asp Leu Lys Gln Gln Ile  Asn Asn Tyr Asn Glu A 430                        450                        470
ATACATCTTCTAATAATAATTTAAGTATATCTCAATTACTTGAGGGAAATACAAATTTTA
sn Thr Ser Ser Asn Asn Asn Leu Ser Ile  Ser Gln Leu Leu Glu Gly Asn Thr Asn Phe I
```

TABLE 13-continued

Nucleotide sequence and derived amino acid sequence of the malaria-specific insert of clone 41-14.

```
          490                510                530
TAAATATTTCTAATACATTTATTAATACGAATTATTCTAATGATTTTCATCA
le Asn Ile Ser Asn Thr Phe Ile Asn Thr Asn Tyr Ser Asn Asp Phe His
```

TABLE 14

Nucleotide sequence and derived amino acid sequence of the malaria-specific insert of clone 41-15.

```
       10                    30                    50
ACAGCAACAACAATAATAATAATAATAATAATATTAGTAATAATATTAGTAATAATAAAG
 Ser Asn Asn Asn Asn Asn Asn Asn Asn Asn Ile Ser Asn Asn Ile Ser Asn Asn Lys A 70                   90                   110
ATTGTGATGAATACGATTATCAGGAAGAATATTTGAAAGATAAAGCATTATACGATTCAG
sp Cys Asp Glu Tyr Asp Tyr Gln Glu Glu Tyr Leu Lys Asp Lys Ala Leu Tyr Asp Ser A 130                  150                  170
ATATGGACGAAAATACAAATCAACTTCACAATAATGAACATCATACAAATCAACATCACG
sp Met Asp Glu Asn Thr Asn Gln Leu His Asn Asn Glu His His Thr Asn Gln His His A 190                  210                  230
CAAATTGGCATCATCACAAACATCAAAAGCAACATTTCAAACAACTTATTGATCATAACA
la Asn Trp His His His Lys His Gln Lys Gln His Phe Lys Gln Leu Ile Asp His Asn A 250                  270
ATATGATAAATAATAATGATAATAATATTATCAATAA
sn Met Ile Asn Asn Asn Asp Asn Asn Ile Ile Asn
```

TABLE 15

Nucleotide sequence and derived amino acid sequence of the malaria-specific insert of clone 41-17

```
         20                   40                   60
GCACTGCCACCCTTGTTGCGGAAGAATTGCACCAGCTCGGCTATTCACTGGCGCTGGGTC
 Thr Ala Thr Leu Val Ala Glu Glu Leu His Gln Leu Gly Tyr Ser Leu Ala Leu Gly A 80                  100
GCGAAGTAGTTAATGAAAGTAGCCGGATGGGATTACCTGATGAATTC
rg Glu Val Val Asn Glu Ser Ser Arg Met Gly Leu Pro Asp Glu Phe
```

TABLE 16

Nucleotide sequence and derived amino acid sequence of the 5' end of the
P. falciparum (isolate FCBR) gene specified by the insert of the clone 41-2.

```
         10                   30                   50
TTTAAAAATTTTATAAATAATTTTTCTCTTTTATATTTAATACATCTATAAGTATATATG 70                   90                   110
TAATAATTTGATACACAAGAAATGTGTATTTTTAATATATATATATATATATATATATAT 130                  150                  170
ATATATATATATATATATATATATATATATGATATATATAAATATATACATTTATTTA 190                  210                  230
TTCCATAATTTATTAAAAATAAATTTATATATTTTATTTTATTTTTTATTTATTTATTTG 250                  270                  290
TATATATTAAATCTTTTCAATGGAATAAAATTCAATCGGATCGTTATATAAACTTTATTA 310                  330                  350
TATCAAATAAAACACTTTTTATAATAATACGAAAAATATATTTCCTTATTTTTATGTTTT 370                  390                  410
CAAAATTTTAGTAGACTTATAATATTATTATGGATAACATTAACAAATAAAAATATTATG 430                  450                  470
AGTATAATATGTAAATTATTTTTTTTTTTTTACAGTTTATATGTTTATGAACATATAATG 490                  510                  530
TGATAAATAAAATTGATTAATTATTATTATATATAATTACTCTTGTAATTTATTAAAATG 550                  570                  590
GTATATTATATATATATATAATTTTTTTTATATTATTTGAATAAAAATATTAAATAAA 610                  630                  650
AATTTTGTGTTTGGGTAAATCATAATAAGTGCTAACGTTCATAATTTATCTCATTAAAAA
```

TABLE 16-continued

Nucleotide sequence and derived amino acid sequence of the 5' end of the
*P. falciparum* (isolate FCBR) gene specified by the insert of the clone 41-2.

```
          670                    690                    710
ATAGAAATGAAATATAATATTTACGACAGTACATATATATATGTATATTATTAAAAAA 730                    750                    770
AAATAAAAATAACACATATATATATATATATATATATATTGATAATATATATGTTTTA 790                    810                    830
AGTATGGATAAATCAAAAAGTTCCATAGAGAAAGAATTAAATAGGATAAAACAGGATGTG
   Met Asp Lys Ser Lys Ser Ser Ile  Glu Lys Glu Leu Asn Arg Ile  Lys Gln Asp Val 850                    870                    890
AGCTTAAGCGCATTTAGTATCCTCTTTAGTGAAATGGTACAATATTGTTTATATAAAAGT
Ser Leu Ser Ala Phe Ser Ile  Leu Phe Ser Glu Met Val Gln Tyr Cys Leu Tyr Lys Ser 910                    930                    950
AAAAGAGGATATCGAATAGAAGATTGTTTACATGAAATGGGTTTACGTGTAGGTTATAAA
Lys Arg Gly Tyr Arg Ile  Glu Asp Cys Leu His Glu Met Gly Leu Arg Val Gly Tyr Lys 970                    990                    1010
TTAAATGAATATTTAACATATAAGAATAAAGTGAAAAGAAGCATAAATATTATTAATATT
Leu Asn Glu Tyr Leu Thr Tyr Lys Asn Lys Val Lys Arg Ser Ile  Asn Ile  Ile  Asn Ile 1030                   1050                   1070
TTAACATTCATATCTAAACATGTGTGGAAATATTTATTTCAGCATTCATCTGATTTACTT
Leu Thr Phe Ile  Ser Lys His Val Trp Lys Tyr Leu Phe Gln His Ser Ser Asp Leu Leu 1090                   1110                   1130
AAATCTCAAGATAGTATTTATGAGTATATGATATGTGATAAAAATATTTTATTAAATAAA
Lys Ser Gln Asp Ser Ile  Tyr Glu Tyr Met Ile  Cys Asp Lys Asn Ile  Leu Leu Asn Lys 1150                   1170                   1190
TTTATAAATGTACCAAAAGATTATGGAAATATAAATTGTGCTGCCTTTGCAGCAGGTATT
Phe Ile  Asn Val Pro Lys Asp Tyr Gly Asn Ile  Asn Cys Ala Ala Phe Ala Ala Gly Ile 1210                   1230
GTTGAAGGCTTCCTCTGTAGTTCTGAATTC
Val Glu Gly Phe Leu Cys Ser Ser Glu Phe
```

TABLE 17

Nucleotide sequence and derived amino aicd sequence of the 3' end of the
*P. falciparum* (isolate FCBR) gene specified by the insert of the clone 41-2.

```
          1240                   1260                   1280
GAATTCCAAGCAGATGTTACAGCGCACACTATTCATGAAGGCGATGATAATTATAACACT
Glu Phe Gln Ala Asp Val Thr Ala His Thr Ile  His Glu Gly Asp Asp Asn Tyr Asn Thr 1300                   1320                   1340
ACTATTTTTATTAAATTTTATCCGGAAGTAGTGGAAAGAGAAAAAAACCACTAGATATTC
Thr Ile  Phe Ile  Lys Phe Tyr Pro Glu Val Val Glu Arg Glu Lys Asn His 1360                   1380                   1400
ATATAAGGGTCACACAATAAATATATATATATAATACATGTTGTATAAGTTGTCAAAAAA 1420                   1440                   1460
TTTATATGGAAAAAAATAAATTAAATATGTAAATATATATATATATATATATATATATAT 1480                   1500                   1520
TCTTTCTTTCTTTCTTTTTTTTTTTTTTTTGTTATTATTAATGTATTATTTATCCTTATG 1540                   1560                   1580
CATGGGATTATTTAACAAATTTATTGATAAAATAAATGTACCCCTTTTTTTTTTTCTTT 1600                   1620                   1640
TTTTTCTTTTTTTTTTTTTTGTATAAACATATTTATATATATTTATATTTAATTAAACCT 1660                   1680                   1700
TTTTTAACATTTTAAATCTATATGAAATAATAAATGAAGACATGACTATTTTAATACAAG 1720                   1740                   1760
GAAATTAATGGTTCCTTAAATTTCACATAAAAAAAAAAAATAAAACATATAATATATATAT 1780                   1800                   1820
ATATATATATAAAACACTTGGTTCTAATTTTTTTTTTTTTTTTTTTTTTTTTTTTTTAA 1840                   1860                   1880
TTTGTATGGAGATATTATAATATTTAAACAATATATATGACATATATAGAGGACATACTG
```

TABLE 17-continued

Nucleotide sequence and derived amino aicd sequence of the 3' end of the
P. falciparum (isolate FCBR) gene specified by the insert of the clone 41-2.

```
            1900                      1920                      1940
TTACCAATATTTTCAATACATTGTTGGAATTTTTTATTTTTTCATATATCATACATAAGA 1960                      1980                      2000
CCTTCTGGAAAAGAAAAAAGTAATAAAGTGTCTTATATACTATTAATTTTGAATATAGAT 2020                      2040                      2060
TTTTTTTCTTTTCTTTCAAAATTAAAAAGTATTCTATCAATGTATGTAAAATATATAATT 2080                      2100                      2120
TTACTTTTTTTTTGTTCTTTTTTCTATTTTTAAATACGTATGTCCTCGTTTTTTTTTTTT 2140                      2160                      2180
CTTTTTATAACATTATTTTGCATATTCCAAATTTTTTCTATGTGTCCAAAAAAAAAAAAA 2200                      2220                      2240
AAAAAAATAAAGTGTTAATAAAAAAATTAAATAATATATGTGAAGATACTTTTTTTAATA

2260
TGCATATGTATATATATTTATATATATAGATC
```

TABLE 18

Nucleotide sequence and derived amino acid sequence of the 41 kD protein of P. falciparum

```
             10                        30                        50
AATTTTTTTTTTGAATATTCTTTTTAGCATTTGATATAATATTATTTTGAAAATGGTAAG 70                        90                       110
AATATAAAACATTTAAGAAATAAATAAAAGTACAGTGTTTATATATACCGTATAAATGAA 130                       150                       170
TAAGTGTATATATATATATATATATTAAATACATTTATATTATTAATTTATACCAATGCA 190                       210                       230
TAGTTATATATATATACTATTATATATGTATTCATTTTATTCTGCTCACATTATTTAT 250                       270                       290
GCATATGCTTCCTTTATAATAAATATATTCGTATTAACATTCAAGAAATGAGGACGAAAT 310                       330                       350
ATTCCTTAATTTACATATGTATTTTTTTATTAATTGAAAAAAAAAAAAAAAATAGTAAAAA 370                       390                       410
TAAGTATAGGCATATATTGAATAATGTGCTGTTGAATTGATTTATATATATATATATATA 430                       450                       470
TATATGTATATTTATTTATATTTATACATATGGGAATATTATATATTTTCCTTTTTTCTT 490                       510                       530
ATTTTTATATTTTTATATTTTTTTTTAGGCTCATTGCACTGATATATGAATGCCCCAAAA
                                                  Met Asn Ala Pro Lys 550                       570                       590
AAATTACCAGCAGATGTTGCCGAAGAATTAGCAACCACCGCCCAAAAGCTTGTTCAAGCT
Lys Leu Pro Ala Asp Val Ala Glu Glu Leu Ala Thr Thr Ala Gln Lys Leu Val Gln Ala 610                       630                       650
GGAAAGGGAATTTTAGCTGCTGATGAATCAACACAAACCATTAAGAAAAGATTCGACAAC
Gly Lys Gly Ile Leu Ala Ala Asp Glu Ser Thr Gln Thr Ile Lys Lys Arg Phe Asp Asn 670                       690                       710
ATCAAATTAGAGAACACAATAGAAAACAGAGCTAGCTACAGAGATTTATTATTTGGAACT
Ile Lys Leu Glu Asn Thr Ile Glu Asn Arg Ala Ser Tyr Arg Asp Leu Leu Phe Gly Thr 730                       750                       770
AAAGGATTAGGAAAATTCATTTCAGGAGCAATTTTATTTGAAGAAACATTATTTCAAAAG
Lys Gly Leu Gly Lys Phe Ile Ser Gly Ala Ile Leu Phe Glu Glu Thr Leu Phe Gln Lys 790                       810                       830
AATGAAGCCGGTGTACCAATGGTTAATTTATTACACAATGAAAATATAATTCCAGGTATT
Asn Glu Ala Gly Val Pro Met Val Asn Leu Leu His Asn Glu Asn Ile Ile Pro Gly Ile 850                       870                       890
AAGGTTGATAAAGGTTTGGTTAACATTCCATGCACAGATGAAGAAAAATCAACTCAAGGT
Lys Val Asp Lys Gly Leu Val Asn Ile Pro Cys Thr Asp Glu Glu Lys Ser Thr Gln Gly
```

TABLE 18-continued

Nucleotide sequence and derived amino acid sequence of the 41 kD protein of *P. falciparum*

```
       910                     930                    950
TTAGATGGATTAGCAGAAAGATGCAAAGAGTATTATAAAGCTGGTGCAAGGTTTGCTAAA
Leu Asp Gly Leu Ala Glu Arg Cys Lys Glu Tyr Tyr Lys Ala Gly Ala Arg Phe Ala Lys 970                     990                    1010
TGGAGAACAGTTTTAGTTATTGACACAGCCAAAGGAAAACCAACTGATTTATCAATTCAC
Trp Arg Thr Val Leu Val Ile Asp Thr Ala Lys Gly Lys Pro Thr Asp Leu Ser Ile His 1030                    1050                   1070
GAAACTGCATGGGGATTGGCTAGATATGCATCTATTTGTCAACAAAATAGATTAGTTCCA
Glu Thr Ala Trp Gly Leu Ala Arg Tyr Ala Ser Ile Cys Gln Gln Asn Arg Leu Val Pro 1090                    1110                   1130
ATTGTTGAACCTGAAATTTTAGCTGATGGACCACACTCAATTGAAGTTTGTGCAGTTGTA
Ile Val Glu Pro Glu Ile Leu Ala Asp Gly Pro His Ser Ile Glu Val Cys Ala Val Val 1150                    1170                   1190
ACTCAAAAAGTTTTATCATGTGTATTTAAAGCTTTACAAGAAAATGGTGTATTATTAGAA
Thr Gln Lys Val Leu Ser Cys Val Phe Lys Ala Leu Gln Glu Asn Gly Val Leu Leu Glu 1210                    1230                   1250
GGTGCATTGTTAAAACCAAACATGGTTACTGCTGGTTATGAATGTACTGCTAAAACCACT
Gly Ala Leu Leu Lys Pro Asn Met Val Thr Ala Gly Tyr Glu Cys Thr Ala Lys Thr Thr 1270                    1290                   1310
ACTCAAGATGTTGGTTTCTTAACTGTCAGAACCTTAAGGAGAACTGTACCACCAGCCTTA
Thr Gln Asp Val Gly Phe Leu Thr Val Arg Thr Leu Arg Arg Thr Val Pro Pro Ala Leu 1330                    1350                   1370
CCAGGTGTTGTATTTTTATCTGGAGGACAATCAGAAGAAGAGGCTTCTGTTAATTTAAAT
Pro Gly Val Val Phe Leu Ser Gly Gly Gln Ser Glu Glu Glu Ala Ser Val Asn Leu Asn 1390                    1410                   1430
TCAATCAATGCTTTGGGTCCACACCCATGGGCTTTAACCTTCTCTTACGGTAGAGCTTTA
Ser Ile Asn Ala Leu Gly Pro His Pro Trp Ala Leu Thr Phe Ser Tyr Gly Arg Ala Leu 1450                    1470                   1490
CAAGCTTCAGTATTGAACACATGGCAAGGAAAGAAAGAAAATGTTGCAAAGGCAAGAGAA
Gln Ala Ser Val Leu Asn Thr Trp Gln Gly Lys Lys Glu Asn Val Ala Lys Ala Arg Glu 1510                    1530                   1550
GTTTTATTACAAAGAGCTGAAGCCAACTCCTTAGCAACTTATGGTAAATACAAAGGAGGT
Val Leu Leu Gln Arg Ala Glu Ala Asn Ser Leu Ala Thr Tyr Gly Lys Tyr Lys Gly Gly 1570                    1590                   1610
GCAGGTGGTGAAAATGCAGGTGCTTCATTATATGAAAAGAAATATGTCTATTAAAAAACTT
Ala Gly Gly Glu Asn Ala Gly Ala Ser Leu Tyr Glu Lys Lys Tyr Val Tyr 1630                    1650                   1670
CACCAACCAAAAATGAATAATAATAATAATAAATAAATTACTAAATGAATGGTACTATAT 1690                    1710                   1730
TTTTAAAAATAAGGGTAATATATTTCTGTATGTATATATATATATATATATACAAATA 1750                    1770                   1790
TGTGAATATAAAAAAAAAAAAAAAAATGTAATATATATCGATCAATGTATATCTACGATAT

ATAAATATATATTTATTCATATCTCCCTTTTTTAGATGATATATTATAATACCTAAAATT 1870                    1890                   1910
ATATATATTTATTTATTATTATTTTATTTATTTAATAATTTTTTTTTATTAGTAAATGAT 1930                    1950                   1970
AATAAATTTTTTAAACGTTTTTTCAACGTTTTATTAAATGTGTAAATATAAATATAAATA 1990                    2010                   2030
TTATATATATATATATATATATGTATGTATTTATTTATTTATTTATATATACATACAT 2050                    2070                   2090
ACCTGTTGACATTCATGTAATATAATAAAGGAACACATGCTTATTTTGTATTATATATCT 2110                    2130                   2150
TACCTTCTACTTTTTAATAAAAAATGTCAAAGCAGGAAATAAAAACTTTTTAATTTAACC 2170                    2190                   2210
AAAAAAATATAATTAATGATGTACACTTATAGATATTGATACAAGAAAAACATTATATAT 2230                    2250                   2270
GTTTTTTTTTTCTTTCTTTTTTTTTTTTTTTTTTTAATTATAACAAAAAATATTTATTA
```

TABLE 18-continued
Nucleotide sequence and derived amino acid sequence of the 41 kD protein of *P. falciparum*

```
      2290              2310                2330
TAATATATAATTTTAAATGAATGATGCAAATTTAATGAGCCATTTTATTTATATTTTAAA 2350              2370
TAATTATAATAATAACGTACATATATAAAATGGTGATTGAATT
```

We claim:

1. An isolated polypeptide with the amino acid sequence:
ValLysIleLeuLysLysLysLysAsnLeuArgLysIleLys-GluThrThrAspGlu GluLysThrSerAspAsnVal-SerGlnMetTyrGluArgLysGlyGlyProLeuProProProGluLeuArgLys
and partial sequences thereof, said polypeptide and partial sequences thereof being cross-reactive with an antiserum directed to the 41 kD *Plasmodium falciparum* band and capable of providing protection against *Plasmodium falciparum*.

2. An isolated polypeptide as claimed in claim 1, obtained by expression of a sequence of the clone 41-3.

3. Fusion proteins which contain proteins as claimed in claim 1.

* * * * *